United States Patent
Engvall et al.

(10) Patent No.: US 9,492,091 B2
(45) Date of Patent: Nov. 15, 2016

(54) DETECTION OF BLOOD LEAKAGE BY DETECTING A VOLATILE AGENT

(75) Inventors: Daniel Engvall, Halmstad (SE); Patrik Stroemsten, Moelnlycke (SE)

(73) Assignee: REDSENSE MEDICAL AB, Halmstad (SE)

( * ) Notice: Subject to any disclaimer, the term of this patent is extended or adjusted under 35 U.S.C. 154(b) by 616 days.

(21) Appl. No.: 13/882,275

(22) PCT Filed: Oct. 31, 2011

(86) PCT No.: PCT/SE2011/000197
§ 371 (c)(1),
(2), (4) Date: Apr. 29, 2013

(87) PCT Pub. No.: WO2012/057673
PCT Pub. Date: May 3, 2012

(65) Prior Publication Data
US 2013/0217991 A1    Aug. 22, 2013

(30) Foreign Application Priority Data
Oct. 29, 2010   (SE) .................................. 10010650

(51) Int. Cl.
| A61B 5/00 | (2006.01) |
| A61B 5/02 | (2006.01) |
| A61M 1/36 | (2006.01) |
| A61M 5/158 | (2006.01) |

(Continued)

(52) U.S. Cl.
CPC ........... *A61B 5/02042* (2013.01); *A61B 5/145* (2013.01); *A61B 5/445* (2013.01); *A61M 1/3653* (2013.01); *A61M 1/3656* (2014.02); *A61M 5/158* (2013.01); *A61F 2013/0094* (2013.01); *A61F 2013/00412* (2013.01); *A61F 2013/00429* (2013.01); *A61M 2005/1588* (2013.01); *A61M 2205/13* (2013.01)

(58) Field of Classification Search
None
See application file for complete search history.

(56) References Cited

U.S. PATENT DOCUMENTS

| 5,643,589 A | 7/1997 | Chalmers |
| 5,741,509 A | 4/1998 | Kushner |

(Continued)

FOREIGN PATENT DOCUMENTS

| EP | 0 370 600 A1 | 5/1990 |
| WO | 9639923 | 12/1996 |

(Continued)

OTHER PUBLICATIONS

International Search Report for PCT/SE2011/000197, Completed by the Swedish Patent Office on Jan. 31, 2012, 6 Pages.

(Continued)

*Primary Examiner* — Etsub Berhanu
(74) *Attorney, Agent, or Firm* — Birch, Stewart, Kolasch & Birch, LLP

(57) ABSTRACT

A method of detecting bleeding from a wound including: providing, on a support, a substantially non-volatile agent capable of forming a volatile agent on contact with blood; disposing the non-volatile agent on the support at or near the wound; providing a probe for detection of the volatile agent; disposing the probe for detection of the volatile agent at a distance from the support; generating a flow of air in a direction from the support to the probe; monitoring the formation of volatile agent by the probe, thereby detecting a bleeding of the wound. Also disclosed are a system and a disposable device for use in the method.

16 Claims, 1 Drawing Sheet

(51) Int. Cl.
  *A61B 5/145* (2006.01)
  *A61F 13/00* (2006.01)

(56) References Cited

U.S. PATENT DOCUMENTS

| | | |
|---|---|---|
| 6,312,918 B1 | 11/2001 | Ito et al. |
| 6,818,226 B2 | 11/2004 | Reed et al. |
| 2004/0065507 A1* | 4/2004 | Jacobsen .................. E04B 1/84 181/290 |
| 2004/0147038 A1 | 7/2004 | Lewis et al. |
| 2005/0013957 A1* | 1/2005 | Leschinsky .............. B32B 7/06 428/40.1 |
| 2005/0165370 A1 | 7/2005 | Smith et al. |
| 2006/0172002 A1 | 8/2006 | Takada et al. |
| 2007/0023627 A1 | 2/2007 | Finch et al. |
| 2007/0041935 A1 | 2/2007 | Salamone et al. |
| 2007/0142799 A1 | 6/2007 | Ales et al. |
| 2007/0212266 A1* | 9/2007 | Johnston ............... B01L 3/5023 422/400 |
| 2007/0293748 A1 | 12/2007 | Engvall et al. |
| 2008/0056946 A1 | 3/2008 | Ahmad |
| 2009/0082653 A1* | 3/2009 | Rohde ................ A61B 5/02042 600/347 |
| 2010/0152683 A1 | 6/2010 | Lindgren et al. |

FOREIGN PATENT DOCUMENTS

| | | |
|---|---|---|
| WO | 9729735 | 8/1997 |
| WO | 2006001759 | 1/2006 |

OTHER PUBLICATIONS

Lutrasil, "Lutrasil—Skin Friendly and Extremely Soft Spunlaid", Brand Overview, Retrieved from the Internet: URL:http://www.freudenberg-nw.com/en/Company/Brands/Pages/Lutrasil.aspx, retrieved on Apr. 3, 2014, pp. 1-2, XP-002722743.

* cited by examiner

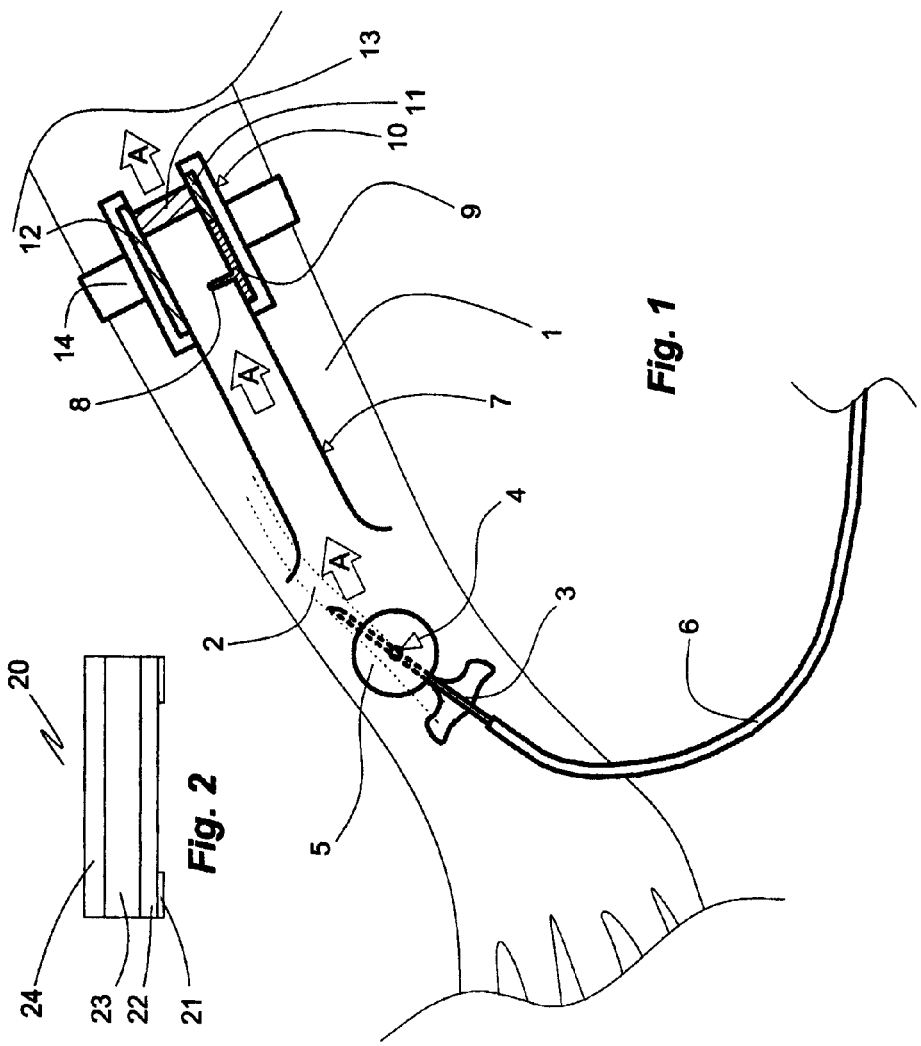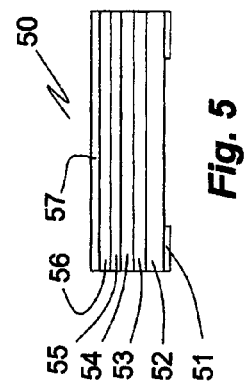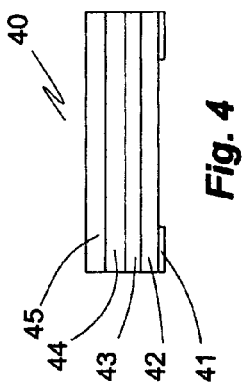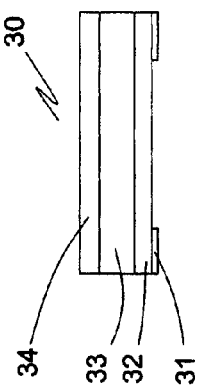

DETECTION OF BLOOD LEAKAGE BY DETECTING A VOLATILE AGENT

CROSS-REFERENCE TO RELATED APPLICATION

This application is the U.S. national phase of PCT Application No. PCT/SE2011/000197 filed on Oct. 31, 2011, which claims priority to Swedish Patent Application No. 1001065-0 filed on Oct. 29, 2010, the disclosures of which are incorporated in their entirety by reference herein.

FIELD OF THE INVENTION

The present invention relates to a method and a system for detecting blood leakage from a wound.

BACKGROUND OF THE INVENTION

A well-recognized problem in hospital care is that wounds caused by surgery or accidents, in spite of having been properly closed and dressed, may start to bleed again. Due to the dressing by which the wound is covered or due to the patient being unconscious or otherwise unable to recognize the bleeding, it is only noticed by the staff and taken care of after a while. In the meantime the patient may have lost a substantial volume of blood. This will no doubt have a detrimental effect on his or her recovery.

Another problem of similar kind is quite frequently seen in blood dialysis. In a life saving treatment patients with impaired or non-existing renal function purify their blood from salts, urea and other metabolic degradation products on a regular basis, such as two or three times per week. In blood dialysis an artery is punctured by a cannula or needle to make a portion of the patient's blood pass through a dialysis apparatus in which it is purified. The purified blood is returned to the patient by venous infusion through a cannula inserted into a large vein. Most often arterio-venous fistula (or a corresponding graft) is created at a patient's wrist or upper arm, from which blood is removed by an arterial cannula and returned downstream by a venous cannula.

A cannula of this kind usually comes with wings extending from a short cylindrical plastic tube in which the cannula is mounted. These wings can be used for securing the cannula by adhesive tape to prevent it from longitudinal displacement in the vein, fistula, or graft. The adhesive tape may accidentally come off and the cannula withdrawn. Inevitably this results in immediate bleeding, which may be quite severe. If the bleeding is not noticed and stopped at once the patient may lose a large volume of blood. Since dialysis patients are usually anaemic, they are particularly affected by such a loss. In addition it is important to prevent blood contained in the dialysis apparatus from being lost if a cannula is removed accidentally. To cope with a loosening arterial needle a safety means is included in known dialysis apparatus. The safety means comprises a pressure sensor disposed on the input side of the apparatus. If the sensor detects a sudden drop in pressure during dialysis the flow of blood through the apparatus is immediately stopped and the personnel alarmed. Due to the pressure drop in the venous needle a loosening thereof cannot be monitored easily in a corresponding manner.

WO 06/001759 A1 discloses a method for detecting blood leakage from a wound in which a sharp bend of an optical fiber is disposed at the wound. Light passing through the fiber is detected at one end of the fiber. Leaking blood contacting the fiber attenuates the passing light. The attenuation, which indicates blood leakage, is detected and an alarm is triggered. The method of WO 06/001759 A1 employs a device comprising an optical fiber and a medical patch. For hygienic reasons the device is disposable.

The provision of alternative methods of detecting blood leakage from a wound not employing a disposable device or a disposable device, which is more economical and/or simpler to manufacture than the prior art device is desirable.

OBJECTS OF THE INVENTION

It is an object of the invention to provide a method and a system of the aforementioned kind, which is safe.

It is another object of the invention to provide a method and a system of the aforementioned kind, of which a disposable device is more economical to manufacture than devices known in the art.

Further objects of the invention will become evident from the following summary of the invention, the description of preferred embodiments thereof illustrated in a drawing, and the appended claims.

SUMMARY OF THE INVENTION

The invention will be explained by reference to a wound caused by insertion of a cannula into a vein. The teaching of the invention is however equally applicable to other kinds of wounds, both surgically and accidentally caused wounds, that have stopped bleeding but are at risk of re-opening and bleeding.

The present invention is based on the insight that detection of a volatile agent formed by leaking blood contacting a substantially non-volatile agent can be used for this purpose.

More specifically, the present invention is based on the insight that a volatile agent can be formed by the reaction of blood with an agent of low volatility, in the following called non-volatile agent, and that the formation of the volatile agent can be detected by a detection means disposed at a distance from the site of formation. The volatile agent is formed by reaction of the water component of blood with the non-volatile agent. In this invention, the non-volatile agent is an agent capable of forming a volatile agent from which it differs in boiling point by at least 100° C., and even by 200° C. or 300° C. or more. The property of low volatility of the non-volatile agent is important, since evaporation of the agent, at least of a substantial amount of it, should be avoided during the monitoring period to avoid compromising monitoring safety. In respect of hemodialysis a monitoring period is, for instance, 5 hours or 7 hours. The amount of non-volatile agent evaporated during the monitoring period should not exceed 20%, preferably it should be less than 10%, most preferred less than 1%.

The volatile agent is transported by diffusion/convection to the detection means. Preferably it is transported to the detection means by controlled convection. Controlled convection is convection controlled in a manner so as to create an air stream from the site of formation of the volatile agent to the site of detection can be produced by a convection producing means. The air stream carries transports the volatile agent from the site of formation to the site of detection. A suitable convection producing means comprises a fan, in particular an electrically driven fan. The convection producing means of the invention may also comprise an air stream conducting means such as a tube disposed intermediate between the site of formation and the site of detection.

The volatile agent can be any agent capable of being transported by an air stream in a gaseous state except for a component of air comprised by oxygen, nitrogen, carbon dioxide, carbon monoxide, water, helium, and argon. While air does additionally contain a great number of other components in amounts varying in respect of the particular environment, such as nitrogen oxides, hydrogen, and methane, their low concentration can be compensated for by setting an appropriate lower concentration limit for detection.

The non-volatile agent is disposed at a wound, such as a wound caused by the insertion of a cannula into a blood vessel, so that it is contacted by blood leaking from the wound within a short period of time upon the onset of leakage, such a within less than 30 seconds and even within less than 10 or 5 seconds. A volatile agent so produced can be detected by a detector sensitive to the agent but essentially insensitive to a component of air or to the volatile agent below a selected detection limit.

Examples of suitable non-volatile agents of the invention are (respective volatile agent formed by contact with an aqueous media such as blood in parenthesis):

$CaC_2$ (acetylene);

$CaH_2$ (hydrogen):

$BaH_2$ (hydrogen);

$NaBH_4$ (hydrogen);

$KBH_4$ (hydrogen);

$NaBH_4$ or $KBH_4$+catalyst, such as a carboxylic acid, $CoCl_2$, aluminum oxide (hydrogen);

$NH_3BH_3$+catalyst, such as $Pd^{2+}$ or cation exchange resin, such as amberlite (hydrogen)

$(NH_4)_2CO_3$ (ammonia);

$NH_4Cl$+base, for instance $Na_2CO_3$ (ammonia); $(NH_4)_2SO_4$+base, for instance $Na_2CO_3$ (ammonia)

a mixed anhydride of an ion exchange resin with carboxylic groups and a low-molecular carboxylic acid, in particular acetic acid (low molecular carboxylic acid);

triethyl carbonate+acid, for instance citric acid (ethanol);

tripropyl carbonate+acid, for instance citric acid (propanol);

$Na_2S$+acid, for instance $NaH_2PO_4$ (hydrogen sulfide).

The non-volatile agent or a matrix comprising the non-volatile agent is attached to a support, in particular a textile woven or non-woven support, such as a cotton pad, a cellulose fiber pad, a synthetic polymer fiber pad, including a pad comprising two or more fiber materials. The pad is attached to the skin at the wound, that is, preferably not in contact with the wound but disposed in its immediate vicinity, such as surrounding the wound fully or partially. Attachment of the pad to the skin can be by, for instance, a medical-grade adhesive.

The catalyst or acid or base can be applied to the support in a manner so as to keep it separate from the non-volatile agent until the support is contacted by blood. An appropriate support is a layered support comprising one or more layers of non-volatile agent and one or more layers of catalyst or base. A layer comprising any of non-volatile agent, catalyst, acid, and base can be protected by disposing it between empty layers.

Alternatively or additionally, the non-volatile agent can be entrapped in a matrix, such as a carbohydrate matrix, or enclosed in a shell readily dissolvable in water, such as a shell of gelatin.

Gas detectors suitable for detection of the volatile agent of the invention are known in the art. Particularly useful are semiconductor based detectors comprising surfaces capable of selective adsorption of the volatile agent.

The invention will now be explained in more detail by reference to preferred embodiments thereof illustrated in a drawing.

SHORT DESCRIPTION OF THE FIGURES

FIG. 1 is a schematic top view of the system of the invention mounted at a person's anterior forearm region, partially sectioned;

FIGS. 2-5 are radially sectioned views of a layered support loaded with the substantially non-volatile agent of the invention.

DESCRIPTION OF PREFERRED EMBODIMENTS

By means of a strap 14 provided with a Velcro® closure (not shown) extending around a patient's forearm the system of the invention shown in FIG. 1 is mounted at the anterior forearm region 1 for detection of a leakage of blood from a wound 4 caused by the insertion of a cannula 3 into a vein 2, such as at an arterial-venous anastomosis. The cannula 3 is connected with a dialyzer (not shown) by means of a flexible tube 6. A layered support 5 loaded with non-volatile agent of the invention is disposed centered above the wound 4. The circular support 5 comprises a top face and a bottom face. The circumference of the bottom face is provided with a medical adhesive by which the support 5 is attached to the skin. The air intake opening of an air stream conducting tube 7 is disposed at a short distance from the support 5 in a cranial direction. A gas detection probe 8 extends into the lumen of the tube 7 near the output opening thereof. The gas detection probe 8 pertains to a gas detector 9 disposed between a casing 10 enclosing a cranial terminal portion of the tube 7 and said terminal portion. The gas detection probe 8 is selectively sensitive to a volatile agent other than a natural component of air (nitrogen, oxygen, carbon dioxide, helium, neon, argon, xenon). When contacted by an agent to which it is sensitive, the probe emits or increases or decreases an electrical signal, which is received and analyzed by the gas detector 9. While trace amounts of hydrogen, hydrogen sulfide, and ammonia can be present in air, their presence is disregarded from or compensated for in the present context. The gas detector 9 comprises a microprocessor and software dedicated to the analysis of the gas detection probe 8 signal. The gas detector 9 including the probe 8 is powered by a battery 12, such as a rechargeable lithium ion battery. Proximally of the probe 8 a fan 13 powered by a DC motor is mounted in the lumen of the tube 7. The fan 13 creates a cranially directed air stream A in the tube 7. Air is sucked in at the air intake opening and expelled at the air output opening after the air stream has passed the gas detection probe 8. A volatile agent released at or from the support 5 will be sucked into the caudal opening of the tube 7 by the air stream generated by the fan 13 and made pass the gas detection probe 8. If the volatile agent is one that has affinity to the gas detection probe 8, that is, is selectively adsorbed by a surface of the probe 8, an electrical signal of the probe 8 is created or amplified or attenuated. The signal or change in signal strength is detected by the detector 9. If the signal or change in signal strength exceeds a preset limit, an alarm produced by an alarm unit 11 is triggered. The alarm may be of a visual and/or audible nature. The visual or audible alarm can be emitted by the alarm unit 11. Alternatively or additionally, the alarm unit 11 can comprise a sender for transmission of a wireless signal to a receiver (not shown) comprising visual and/or audible alarm generating means like a flashing light or a bell or similar. The alarm signal can also be transmitted to a control room from where one or several persons are supervising dialysis patients during dialysis. Alternatively or additionally, the alarm unit 11 can be electrically connected with the dialysis machine (not shown) to which the patient is coupled via one or two cannulae, only one cannula being shown in FIG. 1. This connection allows to stop dialysis as soon as the alarm is triggered.

FIGS. 2 to 5 show supports according to the invention in radial section. Their circular bottom face is provided with a peripheral layer of medical adhesive 21, 31, 41, 51 and so defined. The layers are numbered starting from the bottom layer.

The support 20 of FIG. 2 comprises three layers of non-woven cotton bonded by a polymer melt applied at intersections of a square net pattern. Layers 22 and 24 are empty protective layers. The intermediate layer 23 comprises calcium hydride flakes of a minimum sieved size so as to be firmly held by the cotton threads. Blood reaching the intermediate layer via bottom layer 22 reacts with calcium hydride under formation of hydrogen, which can be detected by a hydrogen-specific gas detection probe.

The support 30 of FIG. 3 comprises a bottom layer 32 and a top layer 34 layers of non-woven cotton interspaced by a central layer 32 of cellulose acetate fiber. The central layer comprises calcium carbide made adherent to the fibers by contacting it with a solution of polyvinyl chloride-vinyl acetate copolymer dissolved in tetrahydrofuran.

Blood reaching the intermediate layer 33 via the bottom layer 32 reacts with calcium carbide under formation of acetylene, which can be detected by an acetylene-specific gas detection probe.

The support 40 of FIG. 4 comprises a bottom layer 42 and a top layer 45 of non-woven cotton interspaced by two layers 43, 44 of same material. Layer 43 comprises citric acid and heparin made to adhere to the fiber by aqueous carboxymethyl cellulose. Layer 44 comprises sodium borohydride deposed on the fiber as from a solution in diglyme. The layers are not bonded; they are kept in the illustrated layered configuration by encasement in form of a net of polypropylene fibers (not shown). Blood reaching the citric acid layer 43 via the bottom layer 42 dissolves the citric acid, the aqueous solution of which is transported to adjacent layer 44 where sodium borohydride is dissolved and reacted with water under formation of hydrogen, which can be detected by a hydrogen-specific gas detection probe.

The support of FIG. 5 comprises a bottom layer 52 and a top layer 57 of a cotton web. The layer 53 abutting the bottom layer is of fluffy non-woven cotton soaked with an aqueous solution of $NaH_2PO_4$ and heparin, then thoroughly dried. The layer 54 on top of the sodium dihydrogen phosphate layer 53 is of an empty cotton web. The layer 55 disposed on top of the layer 54 is of fluffy non-woven cotton soaked with an aqueous solution of sodium sulfide and then thoroughly dried. Blood entering from below the bottom layer 52 and from there the sodium dihydrogen phosphate layer dissolves $NaH_2PO_4$ under formation of an acidic aqueous solution which, after passage through the empty separating layer 54 enters the sodium sulfide layer 56 and dissolves sodium sulfide which is decomposed in the acidic media to hydrogen sulfide and disodium hydrogen phosphate. Hydrogen sulfide evolves as a gas from the solution and can be detected by a hydrogen sulfide-specific gas detection probe.

The invention claimed is:

1. A method of detecting bleeding from a wound, comprising:
providing, on a support, a substantially non-volatile agent capable of forming a gaseous volatile agent given off to the surrounding air on contact with blood;
disposing the non-volatile agent on the support at or near the wound;
providing a probe for detection of the volatile agent from the air surrounding the support;
disposing the probe for detection of the volatile agent at a distance from the support;
generating a flow of air in a direction from the support to the probe; and
monitoring the formation of said volatile agent with the probe, to thereby detect bleeding of the wound.

2. The method of claim 1, wherein the non-volatile agent is calcium hydride, barium hydride, calcium carbide, borohydride, sodium sulfide, ammonium salt, orthoester, $NH_3BH_3$, mixed anhydride of ion exchange resin with carboxylic groups or low-molecular carboxylic acid.

3. The method of claim 2 wherein the non-volatile agent comprises sodium borohydride or potassium borohydride.

4. The method of claim 2 wherein the non-volatile agent comprises an ammonium salt selected from the group of ammonium carbonate, ammonium sulfate, and ammonium chloride.

5. The method of claim 1, further comprising providing an acid, a base, or a catalyst adjacent to said non-volatile agent, said acid, base or catalyst promoting generation of said volatile agent by said non-volatile agent when in contact with blood, thereby enhancing generation of said volatile agent.

6. The method of claim 5, wherein a base provided adjacent to said non-volatile agent, the base being selected from a group consisting of alkali carbonate, alkali hydroxide, dialkali phosphate, trialkali phosphate, and calcium hydroxide.

7. The method of claim 1, wherein the flow of air is generated by a fan.

8. The method of claim 1, wherein the probe is a semiconductor probe.

9. The method of claim 1, wherein the volatile agent is selected from a group consisting of hydrogen, acetylene, methanol, ethanol, hydrogen sulfide, ammonia, and $C_1$-$C_3$ carboxylic acid.

10. A system for detecting bleeding from a wound, comprising:
a substantially non-volatile agent arranged on a support, the non-volatile agent being capable of forming a gaseous volatile agent which is given off to the surrounding air on contact with blood;
a probe for detection of the volatile agent;
a flow generator generating a flow of air from the support to said probe.

11. The system of claim 10, wherein the flow generator is an electrically driven fan.

12. The system of claim 10, comprising a guide, directing the flow of air in a selected direction.

13. The system of claim 12, wherein the guide comprises a tube.

14. The system of claim 10, wherein the non-volatile agent is selected from a group consisting of: calcium hydride, barium hydride, calcium carbide, borohydride, sodium sulfide, ammonium salt, orthoester, $NH_3BH_3$, mixed anhydride of ion exchange resin with carboxylic groups, and low-molecular carboxylic acid.

15. The system of claim 10, wherein the support is layered.

16. The system of claim 10, further comprising at least one of an acid, a base and a catalyst arranged on a layer of the support adjacent to another layer supporting said non-volatile agent.

* * * * *